(12) United States Patent
Liu et al.

(10) Patent No.: US 10,024,770 B2
(45) Date of Patent: Jul. 17, 2018

(54) GAS AUTOSAMPLER

(71) Applicant: INSTITUTE OF BOTANY, THE CHINESE ACADEMY OF SCIENCES, Beijing (CN)

(72) Inventors: Wei Liu, Beijing (CN); Hua Su, Beijing (CN)

(73) Assignee: Institute of Botany of the Chinese Academy of Sciences, Beijing (CN)

(*) Notice: Subject to any disclaimer, the term of this patent is extended or adjusted under 35 U.S.C. 154(b) by 273 days.

(21) Appl. No.: 14/898,729

(22) PCT Filed: Apr. 14, 2015

(86) PCT No.: PCT/CN2015/000259
§ 371 (c)(1),
(2) Date: Dec. 15, 2015

(87) PCT Pub. No.: WO2016/033916
PCT Pub. Date: Mar. 10, 2016

(65) Prior Publication Data
US 2016/0202152 A1    Jul. 14, 2016

(30) Foreign Application Priority Data

Sep. 3, 2014  (CN) .......................... 2014 1 0446243

(51) Int. Cl.
*G01N 1/00* (2006.01)
*G01N 1/24* (2006.01)

(52) U.S. Cl.
CPC ......... *G01N 1/24* (2013.01); *G01N 2001/002* (2013.01); *G01N 2001/242* (2013.01); *G01N 2001/245* (2013.01)

(58) Field of Classification Search
CPC ................................................ G01N 2001/002
See application file for complete search history.

(56) References Cited

U.S. PATENT DOCUMENTS

| | | | |
|---|---|---|---|
| 3,348,658 A | 10/1967 | Cannon | |
| 4,116,067 A * | 9/1978 | Pankratz | G01N 1/24 73/863.31 |
| 6,055,872 A | 5/2000 | Little | |
| 6,840,121 B2 * | 1/2005 | Thomas | G01N 1/14 73/863.31 |
| 2012/0073389 A1 * | 3/2012 | Herve | G01N 9/00 73/864.21 |

FOREIGN PATENT DOCUMENTS

| | | |
|---|---|---|
| CN | 201522479 U | 7/2010 |
| CN | 101949974 A | 1/2011 |
| CN | 102507967 A | 6/2012 |
| CN | 202974959 U | 6/2013 |
| CN | 104198748 A | 12/2014 |
| JP | 2002005913 A | 1/2002 |
| TW | 200708338 A | 3/2007 |

* cited by examiner

*Primary Examiner* — Robert R Raevis
(74) *Attorney, Agent, or Firm* — McCoy Russell LLP

(57) ABSTRACT

The invention discloses a gas autosampler comprising a propeller, a transmission device, a sample chain and a sample feeding cone. As the injector of the present invention is directly used as a sample feeding bottle, the transfer times can be reduced and the pollution possibility can be reduced. Meanwhile, the sample chain can increase and reduce the position number according to the requirements, and the motor controlling can feed the samples for multiple times, so that the samples can be automatically fed.

8 Claims, 3 Drawing Sheets

GAS AUTOSAMPLER

CROSS REFERENCE TO RELATED APPLICATIONS

The present application is a U.S. National Phase of International Patent Application Serial No. PCT/CN2015/000259, entitled "A GAS AUTOSAMPLER," filed on Apr. 14, 2015, which claims priority to Chinese Patent Application No. 201410446243.8, entitled "A GAS AUTOSAMPLER," filed on Sep. 3, 2014, the entire contents of each of which are hereby incorporated by reference for all purposes.

TECHNICAL FIELD

The present invention relates to a gas autosampler, which belongs to a sampler in the field of ecological environment.

BACKGROUND

Unlike the liquid or solid sample, gas sample, when is measured, is fed mainly manually (except online instruments) as the gas sample is more easily lost. Sample feeding is one of the main sources of error of quantitative analysis during gas composition analysis, especially during the manual sample analysis carried by a man. The speed and pressure of sample feeding are different between different operators, and further it is difficult to maintain the consistence between the sample feedings even if by the same operator.

In addition, the sample will go through the steps of collection, transportation and sampling measurement, etc., which are complicated, and most of the steps is implemented by manual work which will introduce a lot of uncertainty. Currently, as one choice, hard bottle is used as a sample bottle to collect and feed sample. The hard bottle is vacuumized before collecting sample, and the sample gas is pressed into the bottle to produce a certain positive pressure in it when the sample is collected. The sample gas is injected into feeding inlet of the equipment under the pressure in the step of sample feeding. However, it is difficult to maintain the pressure in the sample bottle consistent, and different pressures will cause the volume of quantitative ring to be different, which is the leading cause for poor sample repeatability. Further, the container being cleaned incompletely and having poor gas tightness will also affect the results. At present, there has not appeared a kind of low cost, and reliable gas autosampler.

SUMMARY

The present invention aimed to provide a gas autosampler which is suitable for the automatic sample feeding and analysis of the gas sample, and can be connected to the gas analyzer, such as gas chromatograph etc.

The gas autosampler provided by the present invention comprises a propeller, a transmission device, a sample chain and a sample feeding cone.

The propeller comprises a stepping motor I, a screw rod, a sliding block and a cylindrical guide which are sequentially connected, and the sliding block is capable of moving along the cylindrical guide; and on the sliding block, an L-shaped pressing block is connected.

The transmission device comprises a stepping motor II and a driving gear connected together, wherein the driving gear cooperates with a driven gear by means of a belt, and the driven gear is connected with a transmission gear by means of a transmission shaft.

The sample chain comprises at least one cylinder. A spring hoop is fixed on one end of the cylinder. The cylinder is arranged in a gear position of the transmission gear. An injector is fixed on the other end of the spring hoop. An outlet of the injector passes through the cylinder and extends to the other end of the cylinder.

One end of the L-shaped pressing block is capable of pushing a push rod of the injector and pressing a one-way valve connected with the outlet of the injector into the cone of the sample feeding cone.

In the gas autosampler, a long arm end of the L-shaped pressing block is connected to the sliding block.

In the gas autosampler, a two-way valve is connected to the outlet of the injector, wherein the two-way valve is used to control the injector for opening and closing, and the one-way valve is used to control gas for only exporting not importing.

In the gas autosampler, the sample chain comprises several cylinders arranged in the manner of straight chain or endless chain to realize continuously sample feeding.

In the gas autosampler, two adjacent cylinders are arranged in parallel which are connected transversely via connecting sheets at both ends thereof, and then secured by circlips, that is to say, the connections between a plurality of cylinders can be realized via alternate overlaying of the connecting sheets.

In the gas autosampler, the gas autosampler further comprises a tabletting. The tabletting comprises a stainless steel sheet and a spring bolt.

The stainless steel sheet presents in an arc shape which can match the transmission gear.

One end of the stainless steel is fixed on the shell of the gas autosampler, and the other end is connected to the spring bolt. The spring bolt is fixed on the shell of the gas autosampler. The sample chain is compressed by the tabletting.

In the gas autosampler, a through hole is disposed on cone hole of the sample feeding cone. A select valve is connected through the through hole. The number of hole positions of the select valve can be adjusted according to the requirements, and the outlet of the select valve can connect different sample feeding inlets of the instrument, and switch according to the requirements.

In the gas autosampler, a contact switch disposed on the sample feeding cone is triggered when the one-way valve communicated with the outlet of the injector is pressed to the cone tip of the sample feeding cone.

The gas autosampler provided in present invention has the following advantages: the gas autosampler according to the present invention controls the driving distance accurately by using the stepping motor, and both the speed and the distance are adjustable, ensuring the consistence of the sample feeding; according to the present invention, the injector is directly used as a sample feeding bottle, thereby reducing the transfer times and reducing the pollution possibility; meanwhile, the sample chain is capable of increasing and reducing the gear number according to the requirements; and the motor controlling can feed the samples for multiple times, so that the samples can be automatically fed as an unattended operation.

BRIEF DESCRIPTION OF THE DRAWINGS

FIGS. 4A-B are a schematic diagram of the transmission device of the gas autosampler according to the present invention, wherein FIG. 4A is a top view, and FIG. 4B is a front view.

FIGS. 5A-B are a schematic diagram of the connection between the sample feeding cone and the select valve in the gas autosampler according to the present invention, wherein FIG. 5A is a perspective view, and FIG. 5B is a plan view.

THE REFERENCE NUMBERS LIST 1 propeller,
2 transmission device,
3 sample chain,
4 pressing sheet,
5 sample feeding cone,
6 select valve,
7 injector,
8 one-way valve,
9 shell,
10 two-way valve,
11 stepping motor I,
12 sliding block,
13 cylindrical guide,
14 screw rod,
15 L-shaped pressing block,
16 contact switch,
17 pipeline,
21 transmission gear,
22 stepping motor II,
23 driving gear,
24 belt,
25 driven gear,
26 motor base,
27 transmission shaft,
28 blind nut,
31 cylinder,
32 circlip,
33 connecting sheet,
34 spring hoop,
41 stainless steel sheet,
42 spring bolt.

PREFERRED EMBODIMENTS

The present invention will be further described in combined with appended drawings hereafter. However, the present invention is not limited to the following embodiments.

Figure 1:
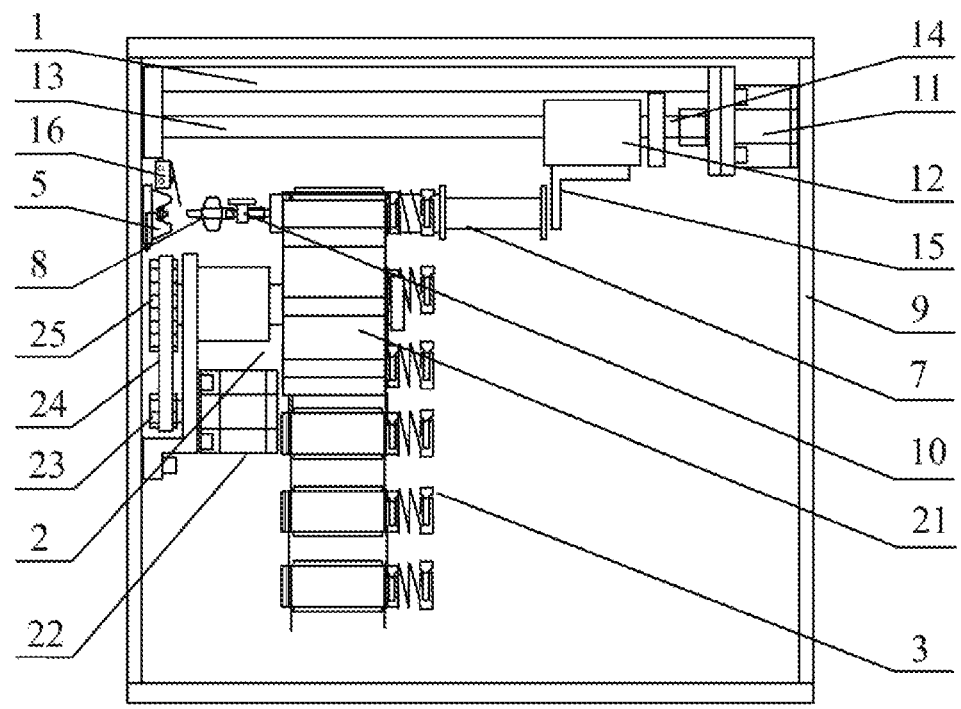
FIG. 1 is a left view of the gas autosampler according to the present invention.
Figure 2:
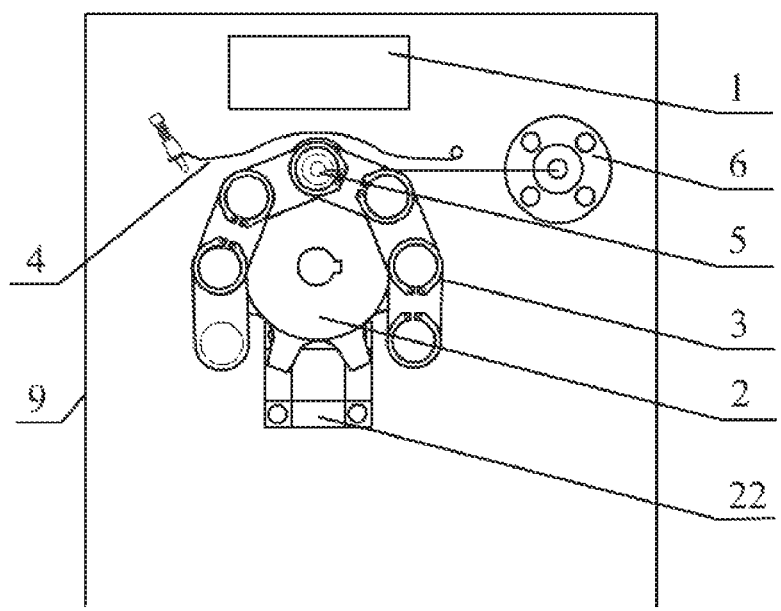
FIG. 2 is a front view of the gas autosampler according to the present invention.

As shown in FIG. 1 and FIG. 2, a gas autosampler provided by the present invention comprises: a propeller 1, a transmission device 2, a sample chain 3, a pressing sheet 4, a sample feeding cone 5, a select valve 6, a injector 7, a one-way valve 8, a shell 9 and a two-way valve 10, wherein the propeller 1 is fixed on the front and the back of the shell, and the transmission device 2 and the sample feeding cone 5 are both fixed on backboard. The sample chain 3 is hung from the transmission device 2, and compressed by the pressing sheet 4.

As shown in FIG. 1, the propeller 1 comprises the stepping motor I 11, the screw rod 14, the sliding block 12 and the cylindrical guide 13 which are sequentially connected, and the sliding block 12 is movable along the cylindrical guide 13. An L-shaped pressing block 15 is connected on the sliding block 12, wherein the longer arm of the L-shaped pressing block 15 is connected to the sliding block 12, and the shorter arm of the L-shaped pressing block 15 can push a push rod of the injector 7 and press the outlet of the injector 7 into the cone tip of the sample feeding cone 5. A contact switch 16 is disposed on the sample feeding cone 5. The outlet of the injector 7 is connected with the two-way valve 10 and the one-way valve 8 in sequence. The contact switch 16 is triggered when the one-way valve 8 is pressed into the cone of the sample feeding cone 5.

Figure 3:
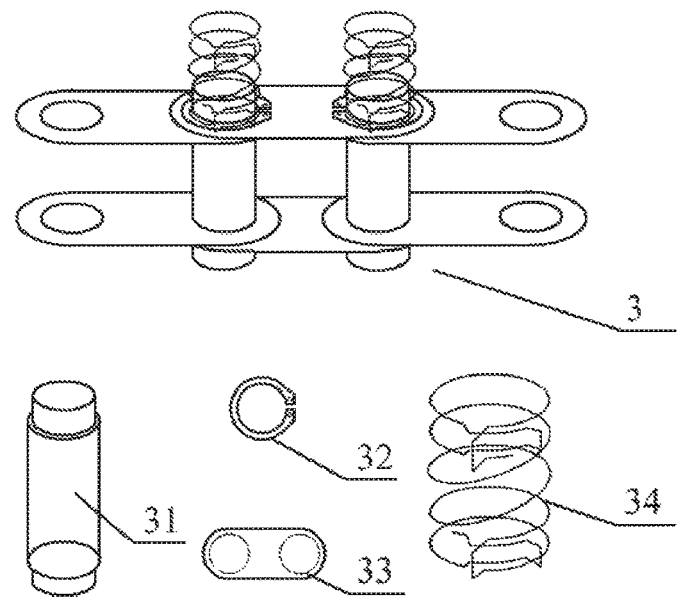
FIG. 3 is an exploded schematic diagram of the sample chain of the gas autosampler according to the present invention.

As shown in FIG. 3, the sample chain 3 comprises several cylinders 31. Two adjacent cylinders 31 are arranged in parallel and are connected on their ends transversely via sheet 33, and then fixed by circlip 32, forming an endless chain arrangement. A spring hoop 34 is fixed on one end of the cylinder 31. The spring hoop 34 is to fix and connect by winding two ends of a spring into a hoop with smaller diameter. The other end of the cylinder 31 is fixed to the injector 7. The outlet of the injector 7 runs through the cylinder 31 and extends to the other end of the cylinder 31. The cylinder 31 can be hung in the gear position of the driving gear 21.

Figure 4A:
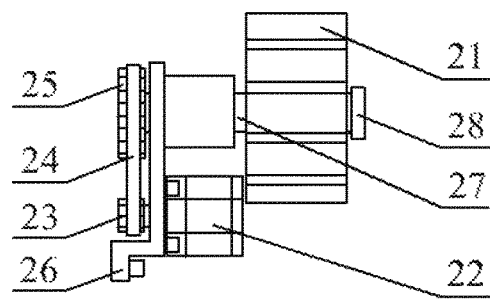
Figure 4B:
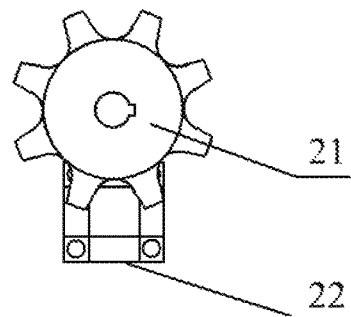

As shown in FIG. 4, the transmission device 2 comprises the stepping motor II 22 and the driving gear 23 that are connected with each other. The driving gear 23 is matched with the driven gear 25 via the belt 24. The driven gear 25 is connected with the transmission gear 21 via the transmission shaft 27. The stepping motor II 22 and the transmission shaft 27 are fixed to the front side of the base 26. The transmission gear 21 is connected to the transmission shaft 27 via key connection to realize axial-moveable connection. The top of the transmission shaft 27 is connected to the blind nut 28 via the threads.

Figure 5A:
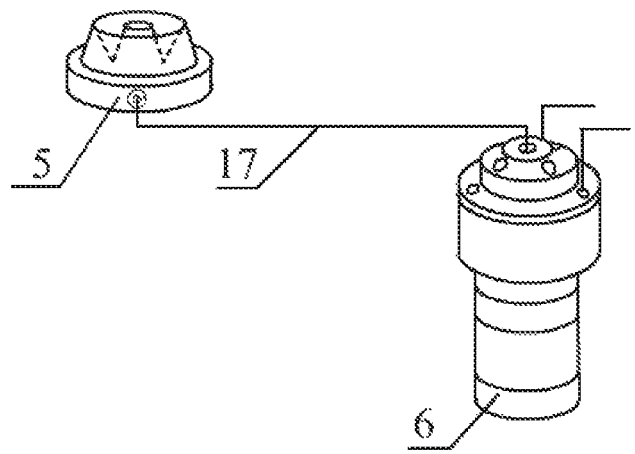
Figure 5B:
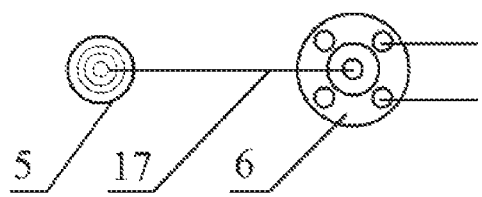

As shown in FIG. 5, the sample feeding cone 5 is a cone structure with a hole in the centre of the circle. An O-ring is surrounded on the outside of the cone tip for sealing. The cone tip is used to hold the outlet of the one-way valve 8 connected with the injector 7. The cone hole of the sample feeding cone 5 leads to the side of the base along the pipeline 17 through a through hole in the side wall, and can be communicated with the gas inlet of an instrument or the select valve 6 through the pipeline 17. The number of hole positions in the select valve 6 can be varied according to the requirements. The outlet of the select valve 6 can connect different sample feeding inlets of the instrument, and switch according to the requirements.

Figure 6:
FIG. 6 is an exploded schematic diagram of the pressing sheet in the gas autosampler according to the present invention.

As shown in FIG. 6, the pressing sheet 4 comprises a stainless steel sheet 41 and a spring bolt 42. The middle section of the stainless steel sheet 41 is arched into an arc which matches the transmission gear 21. One end of the stainless steel sheet 41 rolls into a cylinder which is fixed on the backboard by a bolt, and can rotate up and down. The other end of the stainless steel sheet 41 has a gap for cooperating with the spring bolt 42 for compressing the sample chain 3.

With the gas autosampler according to the present invention, firstly, the outlet of the sample feeding cone 5 is connected with the sample feeding inlet of the instrument, or with the select valve 6 which is in turn connected with the various sample feeding inlets of the instrument one by one.

Assembling the Sample Chain 3

Firstly one connecting sheet 33 is slipped over each ends of two cylinders 31. Then two connecting sheets 33 sequentially are slipped over the ends for connecting one more cylinder 31. This operation is repeated until the number of sample positions meets the requirements, or until the sample chain may be made into circular shape for continuous use.

Sample Filling

Gas sample is pumped into the injector 7, the front end of which is equipped with a one-way valve 8 for exhaust gas. The gas in the one-way valve 8 is evacuated. The injector is inserted into the sample chain 3 by pinching the hand shank of the spring hoop 34, such that the injector is locked on the sample chain 3 by the spring hoop 34. All of the samples are installed in succession.

Pressing Chain

The sample chain 3 is hung into a corresponding gear position of the transmission gear 21. The stainless steel sheet 41 is pressed and locked by the spring bolt 42. The spring bolt 42 is rotated for adjusting the degree of tightness.

Self-Checking

Software controls the stepping motors to complete the self-checking. The stepping motor I 11 rotates the driving screw rod 14 which in turn move the L-shaped pressing block 15 on the sliding block 12 to the outermost for resetting. The stepping motor II 22 transmits the torque of the driving gear 23 connected thereto to the driven gear 25 via the belt 24, and rotates the transmission gear 21 via the transmission shaft 27, which correspondingly drives the sample chain 3 to complete the operation of sample feeding or sample withdrawing. The self-checking of the stepping motor II 22 requires the transmission gear 21 completing one rotation and back to the home position. The self-checking is completed after two stepping motors pass the self-checking.

Setting

After accomplishing the prepare work, the number of the current hole position, the type of sample chain (straight chain or endless chain), the number of the sample chain positions, the name of sample, deepness of sample feeding, times of sample feedings, and the outlet of select valve should be set in the control software.

Sample Feeding

The software controls the stepping motor II 22 to drive the transmission gear 21 based on the setup parameter, thereby moving the hole position of the required sample chain 3 to the sample feeding cone 5. Then the stepping motor I 11 is driven to move the L-shaped pressing block 15 on the sliding block 12 inwardly, such that the pressing block 12 pushes the injector 7 inwardly. The contact switch 16 is triggered when the outlet of the one-way valve 8 connected with the injector 7 compresses the cone tip of the sample feeding cone 5. The contact switch transmits the signal to the software for computing the deepness pushed. The gas is injected into the sample inlet when the pressure in the injector 7 reaches the opening pressure of the one-way valve 8. The select valve switches the openings according to setting. The stepping motor I 11 is stopped when the deepness pushed meets the requirement. Then the software transmits the signal to the instrument for analyzing the sample feeding and continues to control the stepping motor I 11 to accomplish the operation of moving the L-shaped pressing block 15 to the outermost to reset. Meanwhile, the injector 7 is pushed away from the sample feeding cone 5 by the spring hoop 34. After accomplishing the sample analysis, the software drives the stepping motor II 22 to implement the operation of sample feeding for the next sample.

INDUSTRY APPLICATION

The gas autosampler according to the present invention controls the driving distance accurately by using the stepping motor, and both the speed and the distance are adjustable, ensuring the consistence of the sample feeding; according to the present invention, the injector is directly used as a sample feeding bottle, thereby reducing the transfer times and reducing the pollution possibility; meanwhile, the sample chain is capable of increasing and reducing the gear number according to the requirements; and the motor controlling can feed the samples for multiple times, so that the samples can be automatically fed as an unattended operation.

What is claimed is:
1. A gas autosampler, comprising:
a propeller, a transmission device, a sample chain, and a sample feeding cone;
wherein the propeller comprises a first stepping motor, a screw rod, a sliding block, and a cylindrical guide which are sequentially connected, the sliding block moveable along the cylindrical guide, and an L-shaped pressing block connected on the sliding block;
wherein the transmission device comprises a second stepping motor and a driving gear which are connected together, the driving gear matched with a driven gear by means of a belt, and the driven gear connected with a transmission gear by means of a transmission shaft;
wherein the sample chain comprises at least one cylinder on one end of which is fixed with a spring hoop, the cylinder arranged in a gear position of the transmission gear, an injector fixed on the other end of the spring hoop, and an outlet of the injector passing through the cylinder and extending to the other end of the cylinder; and
wherein one end of the L-shaped pressing block pushes a push rod of the injector and presses a one-way valve connected with the outlet of the injector into a cone of the sample feeding cone.

2. The gas autosampler of claim 1, wherein a longer arm of the L-shaped pressing block is connected with the sliding block.

3. The gas autosampler of claim 1, wherein a two-way valve is connected to the outlet of the injector.

4. The gas autosampler of claim 1, wherein the sample chain comprises several cylinders arranged in an arrangement of straight chain or endless chain.

5. The gas autosampler of claim 4, wherein each two adjacent cylinders of the cylinders are arranged in parallel and are connected transversely via sheets on their ends, and secured by circlips.

6. The gas autosampler of claim 1, further comprising:
a tabletting which comprises a stainless steel sheet and a spring bolt;
wherein the stainless steel sheet is in an arc form which is matchable to the transmission gear; and
wherein one end of the stainless steel sheet is fixed on a shell of the gas autosampler, and the other end is connected with the spring bolt, which is fixed on the shell of the gas autosampler.

7. The gas autosampler of claim 1, wherein a through hole is disposed on a cone hole of the sample feeding cone, which is connected to a select valve through the through hole.

8. The gas autosampler of claim 1, wherein a contact switch arranged on the sample feeding cone is triggered when the one-way valve in communication with the outlet of the injector is pressed into a cone tip of the sample feeding cone.

* * * * *